United States Patent
Musa et al.

(10) Patent No.: US 7,132,115 B2
(45) Date of Patent: **\*Nov. 7, 2006**

(54) MODIFIED CARRIER PARTICLES FOR USE IN DRY POWDER INHALERS

(75) Inventors: Rossella Musa, Parma (IT); Roberto Bilzi, Parma (IT); Paolo Ventura, Parma (IT); Paolo Chiesi, Parma (IT)

(73) Assignee: Chiesi Farmaceutici S.p.A., Parma (IT)

( * ) Notice: Subject to any disclaimer, the term of this patent is extended or adjusted under 35 U.S.C. 154(b) by 0 days.

This patent is subject to a terminal disclaimer.

(21) Appl. No.: 10/628,453

(22) Filed: Jul. 29, 2003

(65) Prior Publication Data

US 2004/0096516 A1 May 20, 2004

Related U.S. Application Data

(62) Division of application No. 09/926,105, filed as application No. PCT/EP00/01773 on Mar. 2, 2000, now Pat. No. 6,641,844.

(30) Foreign Application Priority Data

Mar. 5, 1999 (IT) .............................. MI99A0455

(51) Int. Cl.
*A61K 9/14* (2006.01)
*A61K 9/00* (2006.01)
*A61K 9/72* (2006.01)

(52) U.S. Cl. ................. 424/499; 424/400; 424/489

(58) Field of Classification Search ................ 424/400, 424/489, 490, 499
See application file for complete search history.

(56) References Cited

U.S. PATENT DOCUMENTS

| 6,153,224 | A | * | 11/2000 | Staniforth | 424/490 |
| 6,284,287 | B1 | * | 9/2001 | Sarlikiotis et al. | 424/689 |
| 6,528,096 | B1 | | 3/2003 | Musa et al. | |
| 6,641,844 | B1 | * | 11/2003 | Musa et al. | 424/489 |

FOREIGN PATENT DOCUMENTS

| DE | 44 25 255 | 1/1996 |
| GB | 2 107 715 | 5/1983 |
| WO | WO 95/11666 | 5/1995 |
| WO | WO 96/23485 | 8/1996 |
| WO | WO 00/28979 | 5/2000 |

OTHER PUBLICATIONS

Herbert A. Lieberman et al, *Pharmaceutical Dosage Forms*, vol. 2, 1981, Marcel Dekker, Inc., pp. 29-43.

* cited by examiner

Primary Examiner—Michael G. Hartley
Assistant Examiner—Simon J. Oh
(74) Attorney, Agent, or Firm—Oblon, Spivak, McClelland, Maier & Neustadt, P.C.

(57) ABSTRACT

The invention relates to carrier particles for use in pharmaceutical compositions for the pulmonary administration of medicaments by means of dry powder inhalers. In particular, the invention relates to a novel technological process for obtaining a carrier modified so as to improve the efficiency of redispersion of active particles and hence increase the respirable fraction. After the treatment of the invention, the surface of said modified carrier particles can also be coated with a suitable additive so as to further improve the respirable fraction.

12 Claims, 1 Drawing Sheet

MODIFIED CARRIER PARTICLES FOR USE IN DRY POWDER INHALERS

BACKGROUND OF THE INVENTION

Field of the Invention

Figure 1:
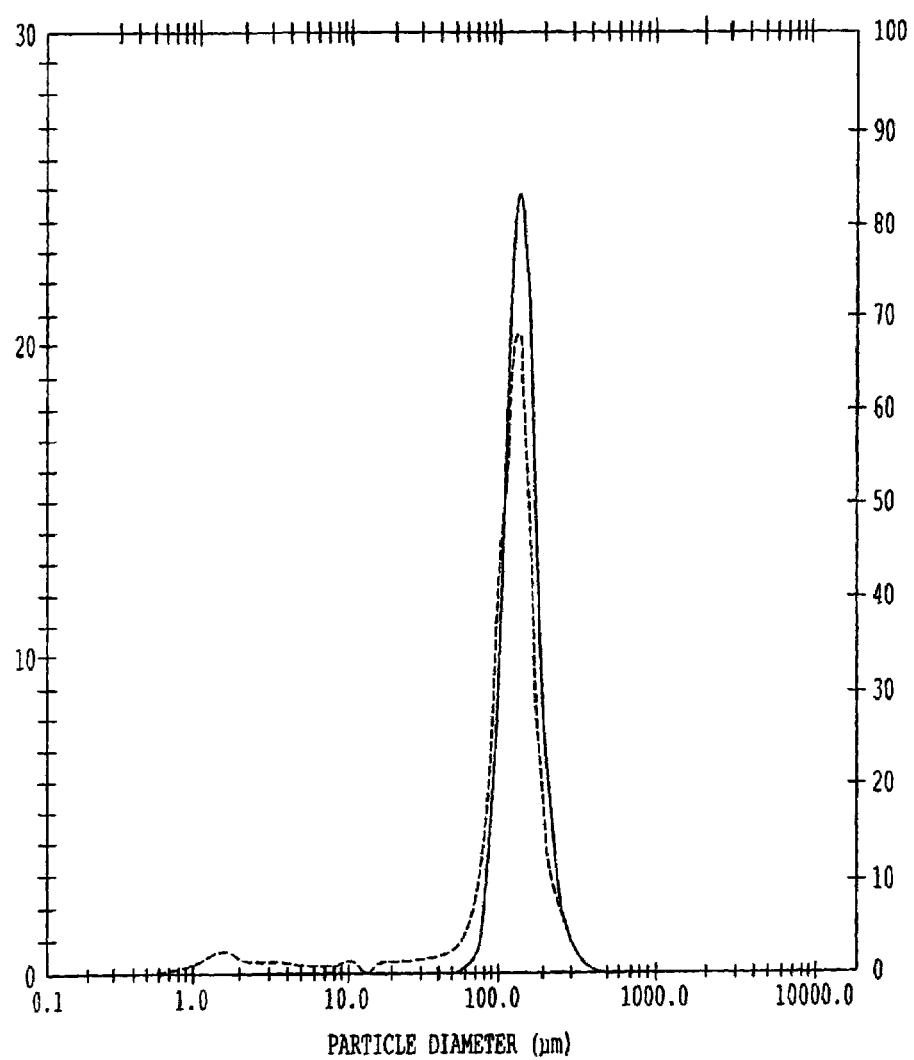

Inhalation anti-asthmatics are widely used in the treatment of reversible airway obstruction, inflammation and hyperresponsiveness.

Presently, the most widely used systems for inhalation therapy are the pressurised metered dose inhalers (MDIs) which use a propellant to expel droplets containing the pharmaceutical product to the respiratory tract.

However, despite their practicality and popularity, MDIs have some disadvantages:

i) droplets leaving the actuator orifice could be large or have an extremely high velocity resulting in extensive oropharyngeal deposition to the detriment of the dose which penetrates into the lungs;

ii) the amount of drug which penetrates the bronchial tree may be further reduced by poor inhalation technique, due to the common difficulty of the patient to synchronise actuation form the device with inspiration;

iii) chloroflourocarbons (CFCs), such as freons, contained as propellants in MDIs, are disadvantageous on environmental grounds as they have a proven damaging effect on the atmospheric ozone layer.

Dry powder inhalers (DPIs) constitute a valid alternative to MDIs for the administration of drugs to airways. The main advantages of DPIs are:

i) being breath-actuated delivery systems, they do not require co-ordination of actuation since release of the drug is dependent on the patient own inhalation;

ii) they do not contain propellants acting as environmental hazards;

iii) the velocity of the delivered particles is the same or lower than that of the flow of inspired air, so making them more prone to follow the air flow than the faster moving MDI particles, thereby reducing upper respiratory tract deposition.

DPIs can be divided into two basic types:

i) single dose inhalers, for the administration of pre-subdivided single doses of the active compound;

ii) multidose dry powder inhaler (MDPIs), pre-loaded with quantities of active ingredient sufficient for multiple doses; each does is created by a metering unit within the inhaler.

Drugs intended for inhalation as dry powders should be used in the form of mironised powder so they are characterized by particles of few micron particle size (μm). Said size is quantified by measuring a characteristic which indicates the capability of the particles of being transported suspended in an air stream. Respirable particles are generally considered to be those with diameters from 0.5 to 6 μm, as they are able of penetrating into the lower lungs, i.e. the bronchiolar and alveolar sites, where absorption takes place. Larger particles are mostly deposited in the oropharyngeal cavity so they cannot reach said sites, whereas the smaller ones are exhaled.

Although micronisation of the active drug is essential for disposition into the lower lungs during inhalation, it is also known that the finer the particles, the stronger are the cohesion forces. Strong cohesion forces hinder the handling of the powder during the manufacturing process (pouring, filling). Moreover they reduce the flowability of the particles while favoring the agglomeration and/or adhesion thereof to the walls. In multidose DPI's, said phenomena impair the loading of the powder from the reservoir to the aerosolization chamber, so giving rise to handling and metering accuracy problems.

Said drawbacks are also detrimental to the respirable fraction of the delivered dose being the active particles unable to leave the inhaler and remaining adhered to the interior of the inhaler or leaving the inhalers as large agglomerates; agglomerated particles, in turn, cannot reach the bronchiolar and alveolar sites of the lungs. The uncertainty as to the extent of agglomeration of the particles between each actuation of the inhaler and also between inhalers and different batches of particles, leads to poor dose reproducibility as well.

In an attempt to improve both the handling and the efficiency, the dry powders for inhalation are generally formulated by mixing the mironised drug with a carrier material (generally lactose, preferably α-lactose monohydrate) consisting of coarser particles. In such ordered mixtures, the micronised active particles, because of the electrostatic or Van der Waals interactions, mainly adhere to the surface of the carrier particles whilst in the inhaler device; on the contrary, during inhalation, a redispersion of the drug particles from the surface of the carrier particles occurs allowing the formers to reach the absorption site into the lungs.

Nevertheless, the use of a carrier is not free of drawbacks in that the strong interparticle forces between the two ingredients may prevent the separation of the micronised drug particles from the surface of the coarse carrier ones on inhalation, so compromising the availability of the drug to the respiratory tract. The surface of the carrier particles is, indeed, not smooth but as asperities and clefts, which are high energy sites on which the active particles are preferably attracted to and adhere more strongly; because of such strong interparticle forces, they will be hardly leave the surface of the carrier particles and be dispersed in the respiratory tract. Therefore, the features of the carrier particles should be such as to give sufficient adhesion force to hold the active particles to the surface of the carrier particles during manufacturing of the dry powder and in the delivery device before use, but that force of adhesion should be low enough to allow the dispersion of the active particles in the respiratory tract.

The prior art discloses several approaches for manipulating the interparticle interactions between the drug and the carrier in ordered powder mixtures.

First, the carrier particles can be chosen according to their median particle size, taking into account the fact that a decrease in median particle size increases the adhesion force between drug and carrier particles.

GB 1,242,211 and GB 1,381,872 disclose pharmaceutical powders for the inhalatory use in which the micronised drug (0.01–10 μm) is mixed with carrier particles of sizes 40 to 80 μm and 80 to 150 μm, respectively; said mixtures can also contain a diluent of the same particle size as the micronised drug.

The deaggregation of the active ingredient from the carrier during inhalation can also be made more efficient by modifying the surface properties of the carrier and/or by addition of a fine fraction (<10 μm), preferably of the same material of the carrier (Podczeck F. *Aerosol Sci. Technol.* 1999, 31, 301–321; Lucas P et al *Resp. Drug Deliv.* 1998, VI, 243–250).

GB 2,240,337 A discloses, for example, a controlled crystallization process for the preparation of carrier particles with smoother surfaces, and, in particular, characterized by a rugosity of less than 1.75 as measured by air permeatry; in practice their smoothness is readily apparent under electronic microscope examination. The use of said carrier particles allows to increase the respirable fraction of the drug (Kassem, Doctoral thesis of the London University, 1990).

EP 0,663,815 claims the use of carriers for controlling and optimizing the amount of delivered drug during the aerosolisation phase, consisting of suitable mixtures of particles of size >20 μm and finer particles (<10 μm).

Staniforth et al. (WO 95/11666) combine both the aforementioned teachings (i.e. modification of the surface properties of the carrier and addition of a fine fraction) by exploiting the effects of a milling process, preferably carried out in a ball mill, referred to as corrasion either the effect of the wind on rocks and the filling of valley with stones during the ice age). Said process modified the surface properties and it gets rid of the waviness of the carrier particles by dislodging any asperities in the form of small grains without substantially changing the size of the particles; the small grains, in turn, can be reattached to the surfaces of the particles wither during the milling phase or after preventive separation followed by mixing, in order to saturate other high energy sites such as clefts. Said preliminary handling of the carrier causes the micronised drug particles to preferably link to the lower energy sites, thus being subjected to weaker interparticle adhesion forces.

Podceck (*J. Adhesion Sci. Technol.* 1998, 12, 1323–1339), after having studied the influence of the corrasion process on the adhesion forces by blending the carrier with different percentages of fine particle fraction before addition of the drug, concluded however that such process is not always sufficient to ensure effective redispersion but the latter also depends on the initial surface roughness of the coarse carrier particles.

Patent literature also suggests the use of powder formulations for inhalation wherein the adhesion between the carrier particles and the active ingredient particles is further reduced by addition of suitable amounts of suitable additives.

BRIEF DESCRIPTION OF THE DRAWING

FIG. 1 shows the of particle size distribution after Malvern analysis of the carrier particles before and after pretreatment in a mixer.

In WO 96/23485, particles are mixed with an anti-adherent or anti-friction material consisting of one or more compounds selected from amino acids (preferably leucine); phospholipids or surfactants; the amount of additive and the process of mixing are preferably chosen in such a way as to not give rise to a real coating, but instead a partial coating directed to the high energy sites. The carrier particles blended with the additive are preferably subjected to the corrasion in a ball mill as disclosed in WO 95/11666.

OBJECT OF THE INVENTION

It has now been found, and it is the object of the invention, that is possible to modify the surface properties of the carrier particles and simultaneously modulate their interaction with the micronised drug particles by producing in situ a fine fraction of the carrier itself, without submitting the coarse carrier particles to a milling process but by employing a conventional mixer.

The use of a mixer, which intrinsically assures milder conditions, allows to modify the surface properties of the carrier particles without significantly changing their sizes, crystalline structure and chemico-physical properties.

It has been indeed reported that the chemical compounds preferably used as carrier, such as lactose, can undergo chemico-physical alterations, when subjected to mechanical stresses, such as milling (Otsuka et al. J. Pharm. Pharmacol. 43, 148–153, 1991).

Moreover, hard treatments such as corrasion may moderately reduce the cristallinity of the additives used (Malcomson R et al. Respiratory Drug Deliv. 1998, VI, 365–367).

It has been also surprisingly found that, by virtue of the milder operative conditions of the invention, the fraction of fine particles of size larger than 10 μm is poor, as proved by the particle size analysis via laser diffractometry (Malvern). It is well known that only the fine fraction below 10 μm, once redistributed onto the surface of the coarse carrier particles, is indeed responsible for the decrease of the interparticle forces, whereas the fine particles of size larger than 10 μm, contribute to decrease the flowability of the powder. Further, the process of the invention yields a fraction of carrier particles whose variation of the starting mean aerodynamic diameter is less than 20%.

On the contrary, milling, as reported above, is a hard process which produces a fine fraction with a much wider particle size distribution which, in turn, could be detrimental for the flow properties of the mixture. Therefore, the powders made with carriers preventatively subjected to milling processes could turn out to be not flowable enough to be suitable for multidose inhalers. Accordingly, the carriers subjected to the milling process often require a further separation step in order to select the fine fraction suitable for being mixed with the coarse carrier particles and discard that one which can be detrimental to the flow properties of the powder.

By operating according to the process of the present invention, the flow properties of the carrier are not significantly affected, as indicated by the Carr index as well as by the Flodex test. the process of the invention allows therefore to avoid the further separation step of the fine fraction suitable for being mixed with the coarse carrier particles.

The mixing process of the invention, compared with the milling process as described in WO 95/11666, allows to remarkably reduce the time of treatment. Ina preferred embodiment of the invention, carriers with suitable properties are indeed obtained after 30 minutes of treatment in a sigma blade mixer whereas, according to WO 95/11666, carrier particles should be milled for at least one hour and preferably six hours.

Finally, the process of the invention provides a carrier for dry powders for inhalation able of giving good performances in terms of respirable fraction of the drug as demonstrated by the examples reported.

Advantageously, the carrier particles are treated in any mixer, of any size and shape, equipped with a rotating element. Preferably the carrier particles are treated in mixers constituted of a stationary or rotating body equipped with any rotatory element (blade, screw) or in the high energy mixers ("high-shear") and blended for a total time ranging from 5 to 360 minutes.

Even more preferably the carrier particles are treated in a sigma-blade mixer at a rate of 100–300 r.p.m. and for 30 minutes.

The carrier particles may be constituted of any pharmacologically acceptable inert material or combination thereof; preferred carriers are those made of crystalline sugars, in particular lactose; the most preferred are those made of α-lactose monohydrate. Advantageously the diameter of the carrier particles lies btween 20 and 1000 µm, preferably between 90 and 150 µm.

A further aspect of the invention relates to the preparation of carrier powders in which, after treatment in a mixer, the carrier particles are mixed with suitable amounts, preferably from 0.05 to 2% by weight, of additives able of further reducing the drug-carrier interparticle forces, thereby increasing the respirable fraction.

The additives can be selected from those belonging to the class of lubricants, such as metal stearates or to the classes of anti-adherent agents or glidants.

The preferred lubricant is magnesium stearate, but stearic acid, sodium stearyl fumarate and sodium benzoate can also be used.

A further aspect of the invention are the formulations for inhalation obtained by mixing the active ingredient particles (with a mean aerodynamic diameter of less than 5 μm with carrier powders obtained according to the process of the invention.

The preferred active particles will be particles of one or mixture of drugs which are usually administered by inhalation for the treatment of respiratory diseases, for example stearoids such as beclomethasone dipropionate, flunisolide and budesonide, β-agonists such as salbutamol, formoterol, salmeterol, terbutaline and corresonding salts; antichloingergics such as ipratropium bromide. Any other active ingredient suitable for pulmonary and/or nasal delivery can be anyway used in these formulations.

EXAMPLES

The process of the invention is illustrated by the following examples.

Example 1 a) Preparation of the Carrier

α-Lactose monohydrate with a starting particle size between 90 to 150 μm is mixed for 30 minutes in a sigma blade mixer. At the end of the treatment, only a slight reduction of the particle size is observed.

The Malvern analysis pattern referring to the particle size distribution of the carrier particles before (- -) and after (----) the pre-mixing treatment is reported in FIG. 1 whereas the relevant data are reported in Table 1.

TABLE 1

| | Particle size distribution (μm) | | |
|---|---|---|---|
| | | Unmixed | Pre-mixed |
| Malvern | d (v, 0.1) | 100.4 | 61.4 |
| | d (v, 0.5) | 138.3 | 127.1 |
| | d (v, 0.9) | 197.8 | 187.7 | b) Preparation of the beclomethasone dipropionate (BDP)/lactose binary mixture

The carrier powder obtained according to the process a) is mixed with such an amount of micronised beclomethasone dipropionate as to obtain a ratio of 200 μm of active to 26 mg total mixture.

c) Characterization of the mixture

The active ingredient/carrier mixture was characterized by its density and flowability parameters.

The poured density (dv) and the tapped density (ds) were calculated as follows. Powder mixtures (20 g) were poured into a glass graduated cylinder and dv was calculated dividing the weight by the volume; ds was calculated from the volume obtained after tapping the powder mixture 500 times using a commercially available apparatus.

The flowability was evaluated from the Carr's index calculated according to the following formula:

$$\text{Carr's index } (\%) = \frac{ds - dv}{ds} \times 100.$$

A Carr index of less than 25 is usually considered indicative of good flowability characteristics.

The flowability properties were also determined by using a Flodex tester. The determination is based upon the ability of the powder mixture to fall freely through holes of different diameters placed at the bottom of a cylinder. The powder was poured into the cylinder via a powder funnel. The flowability index is given in millimeter diameter of the smallest hole through which the powder falls freely.

d) Determination of the aerosol performances.

An amount of powder for inhalation was loaded in a multidose inhaler (Pulvinal$^{(R)}$-Chiesei Pharmaceutical SpA, Italy).

The evaluation of the aerosol performances was performed by using a Twin State Impinger apparatus, TSI (Apparatus of type A for the aerodynamic evaluation of fine particles described in FU IX 4° supplement 1996). The equipment consists of two different glass elements, mutually connected to form two chambers capable of separating the powder for inhalation depending on its aerodynamic size; the chambers are referred to as higher (stage 1) and lower (stage 2) separation chambers, respectively. A rubber adaptor secures the connection with the inhaler containing the powder. The apparatus is connected to a vacuum pump which produces an air flow through the separation chambers and the connected inhaler. Upon actuation of the pump, the air flow carries the particles of the powder mixture, causing them to deposit in the two chambers depending on their aerodynamic diameter. When the air flow is 60 1/min, the aerodynamic diameter limit value, dae, for the deposition in the lower separation chamber is 6.4 μm. Particles with higher dae deposit in Stage 1 and particles with lower dae in Stage 2. In both stages, a minimum volume of solvent is used (30 ml in Stage 2 and 7 ml in Stage 1) to prevent particles from adhering to the walls of the apparatus and to promote the recovery thereof.

The determination of the aerosol performances of the mixture obtained according to the preparation process b) was carried out with the TSI applying an air flow rate of 60 1/min for 5 seconds.

After nebulization of each dose of the dry powder in the Twin Stage Impinger, the apparatus was disassembled and the amounts of drug deposited in the two separation chambers were recovered by washing with a solvent mixture, then diluted to a volume of 50 ml in two volumetric flasks, one for Stage 1 and one for Stage 2, respectively. The amounts collected in the two volumetric flasks were then determined by High-Performance Liquid Chromatography (HPLC). The following parameters, as mean and relative standard deviations (RSD) of the values obtained from three inhalers, by actuating 5 shots from each inhaler, were calculated: i) the fine particle dose (FPD) which is the amount of drug found in stage 1 of TSI; ii) the emitted dose which is the amount of drug delivered from the device recovered in stage 1+stage 2; iii) the fine particle fraction (FPF) which is the percentage of the emitted reaching stage 2 of TSI.

The results in terms of technological parameters and aerosol performances are reported in Table 2, in comparison with a similar preparation obtained by mixing the active ingredient with α-lactose monohydrate lactose 90–150 μm not pre-treated in the mixer (standard preparation).

| | Technological Parameters | |
|---|---|---|
| Apparent Density (g/mL) | Standard Preparation | Preparation of Example 1 |
| Poured | 0.71 | 0.75 |
| Tapped | 0.80 | 0.90 |
| Flodex test (4 mm) | 4 | 4 |
| Flow rate through 4 mm (g/min) | 67 | 46 |
| Carr Index (%) | 11 | 17 |
| | TSI test | |
| Mean weight (mg) | 22.8 (3.3) | 25.6 (2.6) |
| Emitted dose (μg) | 184.0 (3.3) | 165.8 (6.9) |
| FPD (μg) | 31.0 (50.9) | 37.4 (8.9) |
| FPF (%) | 16.9 (53.2) | 22.7 (10.6) |

The results show that the flowability properties of the carrier are not significantly affected even in the presence of a slight reduction of the particle size.

The treatment of the carrier also causes a significant increase of the fine particle fraction (t Student=2.42, p<0.005).

Example 2

Preparation of the salbutamol base/lactose binary mixture

Analogously to what described in example 1, a mixture containing micronised albutamol base as active ingredient in a ratio of 200 μg to 24 mg total mixture was prepared.

The poured and tapped densities and the flowability characteristics were determined as described in example 1. The dry powder for inhalation was loaded in a Pulvinal$^{(R)}$ inhaler and the aerosol performances were determined as described in example 1.

The results are reported in Table 3 in comparison with a similar preparation obtained by mixing the active ingredient with α-lactose monohydrate lactose 90–150 μm not pre-treated in a mixer (standard preparation).

TABLE 3

| | Technological Parameters | |
|---|---|---|
| Apparent Density (g/mL) | Standard Preparation | Preparation of Example 2 |
| Poured | 0.71 | 0.74 |
| Tapped | 0.78 | 0.83 |
| Flodex test (4 mm) | 4 | 4 |
| Flow rate through 4 mm (g/min) | 72 | — |
| Carr Index (%) | 9 | 11 |
| | TSI test | |
| Mean weight (mg) | 22.2 (1.7) | 25.2 (3.3) |
| Emitted dose (μg) | 185.0 (2.6) | 168.2 (4.7) |
| FPD (μg) | 60.1 (11.6) | 80.9 (14.6) |
| FPF (%) | 32.2 (11.5) | 47.9 (11.4) |

Also in this case, the results show that the flowability properties of the carrier do not significantly change.

Analogously, a significant increase (t=9.17, p<0.001) of the fine particle fraction is observed with the carrier prepared according to the process a) described in example 1.

Example 3

Preparation of a BDP/lactose/magnesium stearate ternary mixture

The powder carrier was prepared according to Example 1 a) by mixing α-lactose monohydrate for 30 minutes in a sigma blade mixer. Afterwards lactose was mixed with 0.25% by weight of magnesium stearate in a Turbula mixer for two hours. Finally the dry powder for inhalation was prepared by mixing an amount of micronised beclomethasone dipropionate corresponding to a dose of 200 μg and the carrier (lactose+magnesium stearate) for 30 minutes in a Turbula rotating mixer at 32 rpm.

The poured and tapped densities, the flowability characteristics as well as the aerosol performances were determined as described in example 1.

The results are reported in Table 4 in comparison with a standard formulation obtained by mixing 200 μg of micronised BDP with a carrier powder consisting of 99.75% by weight of α-lactose monohydrate 90–150 μg not pre-treated in a mixer, and 0.25% by weight of magnesium stearate (standard preparation).

TABLE 4

| Standard preparation | Preparation of Example 3 Technological parameters | |
|---|---|---|
| Apparent Density (g/mL) | | |
| Poured | 0.76 | 0.74 |
| Tapped | 0.81 | 0.83 |
| Flodex test (0 4 mm) | 4 | 4 |
| Flow Rate through | | |
| 0 4 mm (g/ml) | 56 | 42 |
| Carr Index (%) | 6 | 10 |
| | TSI test | |
| Mean weight (mg) | 24.5 (1.5) | 27.9 (3.2) |
| Emitted dose (μg) | 188.9 (4.5) | 199.8 (2.2) |
| FPD (μg) | 48.0 (19.5) | 68.9 (5.6) |
| FPF (%) | 25.3 (15.3) | 34.5 (5.2) |

The flowability properties of the carrier do not significantly change even in the presence of a ternary mixture and a significant increase (t=8.29, p<0.001) of the fine particle fraction is observed with the carrier prepared according to the invention.

What is claimed is:

1. A process for the preparation of a dry powder formulation for the pulmonary administration of a micronized drug by means of a dry powder inhaler, said process comprising mixing coarse carrier particles having a diameter which lies between 20 and 1000 μm with fine carrier particles having a diameter of less than 10 μm and magnesium stearate in an amount of 0.05 to 2%, wherein said mixing step is carried out in a sigma blade mixer at a rate of mixing ranging between 100 and 300 r.p.m., for a period of time ranging between 5 to 360 minutes.

2. The process according to claim 1, wherein said coarse carrier particles have a starting diameter between 90 to 150 μm and said fine carrier particles have a mean aerodynamic diameter of less than 10 μm.

3. The process according to claim 1, wherein said mixing is carried out for a time of 30 minutes.

4. The process according to claim 1, wherein said carrier particles consist of one or more saccharides.

5. The process according to claim 1, wherein said carrier particles consist of $\alpha$-lactose monohydrate.

6. The process according to claim 1, which yields a fraction of said carrier particles whose variation of the starting mean aerodynamic diameter is less than 20%.

7. The process according to claim 1, wherein said powder formulation has a Carr's Index of less than 25.

8. A process according to claim 1, wherein after said mixing, one or more active ingredients, whose particles have a mean diameter of less than 5 μm, are added to the carrier.

9. A process according to claim 8, wherein said active ingredient is selected from the group consisting of steroids, $\beta_2$ agonists, anticolinergics, and mixtures thereof.

10. The process according to claim 9, wherein said active ingredient is a $\beta$-agonist selected from the group consisting of salbutamol, formoterol, salmeterol, terbutaline and salts thereof.

11. The process according to claim 9, wherein said active ingredient is a steroid selected from beclomethasone dipropionate, flunisolide, budesonide and the epimers thereof.

12. The process according to claim 9, wherein said active ingredient is an anticolinergic selected from the group consisting of ipratropium bromide and oxytropium bromide.

* * * * *